US00PP14061P29

(12) United States Plant Patent
Dümmen

(10) Patent No.: US PP14,061 P2
(45) Date of Patent: Aug. 12, 2003

(54) GERANIUM PLANT NAMED 'DUEBALILA'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/228,468

(22) Filed: Aug. 27, 2002

(51) Int. Cl.[7] ..... A01H 5/00

(52) U.S. Cl. ..... Plt./332

(58) Field of Search ..... Plt./332

*Primary Examiner*—Kent Bell
(74) *Attorney, Agent, or Firm*—C. A. Whealy

(57) ABSTRACT

A new and distinct cultivar of Ivy Geranium plant named 'Duebalila', characterized by its upright and outwardly spreading plant habit; freely basal branching habit; freely and early flowering habit; and red purple-colored single flowers.

1 Drawing Sheet

BOTANICAL CLASSIFICATION/CULTIVAR DENOMINATION

*Pelargonium peltatum* cultivar 'Duebalila'.

BACKGROUND OF THE INVENTION

The present invention relates to a new and distinct cultivar of Ivy Geranium plant, botanically known as *Pelargonium peltatum*, and hereinafter referred to by the name 'Duebalila'.

The new Ivy Geranium is a product of a planned breeding program conducted by the Inventor in Rheinberg, Germany. The objective of the breeding program was to develop new Ivy Geraniums with attractive flower and foliage colors.

The new Ivy Geranium is an induced mutation of a proprietary selection of *Pelargonium peltatum* identified as code number 94-71-00, not patented. The cultivar Duebalila was discovered and selected by the Inventor as a flowering plant within a population of irradiated plants of the parent selection in Rheinberg, Germany in June, 2000.

Asexual reproductiuon of the new cultivar by terminal vegetative cuttings taken at Rheinberg, Germany since June, 2000 has shown that the unique features of this new Ivy Geranium are stable and reproduced true to type in successive generations of asexual reproduction.

SUMMARY OF THE INVENTION

The following traits have been repeatedly observed and are determined to be the unique characteristics of 'Duebalila'. These characteristics in combination distinguish 'Duebalila' as a new cultivar and distinguish it from other known Ivy Geranium cultivars:

1. Upright and outwardly spreading plant habit.
2. Freely basal branching habit.
3. Freely and early flowering habit.
4. Red purple-colored single flowers.

Compared to plants of the parent, the selection 94-71-00, and the cultivar 'Duebablu', U.S. Plant patent application Ser. No. 10/228,469, plants of the new Ivy Geranium differ in flower color.

The new Ivy Geranium can be compared to plants of the cultivar 'Blizzard Pink', not patented. In side-by-side comparisons conducted in Rheinberg, Germany, plants of the new Ivy Geranium differed from plants of the cultivar Blizzard Pink in the following characteristics:

1. Leaves of plants of the new Ivy Geranium had a zonation pattern whereas leaves of plants of the cultivar Blizzard Pink did not have a zonation pattern.

2. Plants of the new Ivy Geranium had broader umbels with more flowers per umbel than plants of the cultivar Blizzard Pink.

3. Plants of the new Ivy Geranium had larger flowers than plants of the cultivar Blizzard Pink.

4. Flower color of plants of the new Ivy Geranium was darker red purple than flower color of plants of the cultivar Blizzard Pink.

5. Plants of the new Ivy Geranium had longer peduncles than plants of the cultivar Blizzard Pink.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Ivy Geranium. The photograph comprises a side perspective view of typical flowering plants of 'Duebalila' grown in a container.

DETAILED BOTANICAL DESCRIPTION

The cultivar Duebalila has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown with three plants per 10.5-cm container. Plants were about eight weeks from unrooted cuttings when the photographs and the detailed botanical description were taken.

In the following description, color references are made to The Royal Horticultural Society Colour Chart, 1995 edition, except where general terms of ordinary dictionary significance are used.

Botanical classification: *Pelargonium peltatum* cultivar Duebalila.

Parentage: Induced mutation of a proprietary selection of *Pelargonium peltatum* identified as code number 94-71-00, not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About 21 days at 20° C. Winter: About 28 days at 20° C.

*Root description.*—Fine, fibrous; white in color.

*Rooting habit.*—Freely branching.

Plant description:

*General appearance.*—Upright and outwardly spreading plant habit, rounded; densely foliated.

*Growth and branching habit.*—Moderately vigorous. Freely basal branching, about four lateral branches per plant.

*Plant height.*—About 17.5 cm.

*Plant width.*—About 11 cm.

*Lateral branches.*—Length: About 16 cm. Internode length: About 2.5 cm. Texture: Smooth. Color: 144A.

*Foliage description.*—Arrangement: Alternate, single. Quantity of leaves per lateral branch: About six. Length: About 6.9 cm. Width: About 8.6 cm. Shape: Reniform. Apex: Acute. Base: Peltate. Margin: Crenate. Venation pattern: Palmate. Texture, upper and lower surfaces: Smooth; glabrous. Color: Young foliage, upper surface: 137A. Young foliage, lower surface: 144A. Fully expanded foliage, upper surface: 137B. Fully expanded foliage, lower surface: 144A. Venation, upper and lower surfaces: 144A. Zonation pattern: Width: About 7 mm. Color: 137A. Petiole: Length: About 6.3 cm. Diameter: About 1.8 mm. Color, upper and lower surfaces: 144A.

Flower description:

*Flower arrangement.*—Red purple-colored single flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering; at full flower, plants have about four open and developing umbels with about twelve flowers per umbel.

*Flowering season.*—Flowering continuous spring through summer. Early flowering, plants begin flowering about eight weeks after planting.

*Flower longevity.*—Flowers last about five to seven days on the plant.

*Umbel size.*—Height: About 5.5 cm. Diameter: About 12 cm.

*Flower size.*—Diameter: About 5 cm. Depth (height): About 1.5 cm.

*Flower buds.*—Length: About 1.4 cm. Diameter: About 7 mm. Shape: Ovoid. Color: 144A.

*Petals.*—Quantity per flower: About five. Length: About 2.5 cm. Width: About 1.3 cm. Shape: Obovate. Apex: Rounded. Base: Attenuate. Margin: Entire, sinuate. Texture, upper and lower surfaces: Smooth; glabrous. Color: When opening and fully opened, upper surface: 74A; venation towards base, 60A; interveinal areas towards base, close to 155D. When opening and fully opened, lower surface: 67C.

*Petaloids.*—None observed.

*Sepals.*—Quantity per flower: About five, arranged in a single whorl. Length: About 1.6 cm. Width: About 3.5 mm. Shape: Elongated, tapering. Apex: Apiculate. Margin: Entire. Texture, upper and lower surfaces: Smooth; glabrous. Color: upper and lower surfaces: 144A.

*Peduncle* (*umbel stem*).—Length: About 12 cm. Diameter: Less than 1 cm. Angle: Erect. Strength: Moderately strong. Texture: Smooth; glabrous. Color: 144A.

*Pedicel* (*individual flower stem*).—Length: About 3 cm. Diameter: About 1 mm. Angle: Erect. Strength: Moderately strong. Texture: Pubescent. Color: 144A faintly overlain with 178A.

*Reproductive organs.*—Androecium: Anther quantity per flower: About six. Anther length: About 3 mm. Anther shape: Ovate. Anther color: 60A. Pollen amount: Moderate. Pollen color: 28A. Gynoecium: Pistil quantity per flower: One. Pistil length: About 1 cm. Stigma shape: Five-parted, star-shaped. Stigma color: 59A. Style length: About 6 mm. Style color: 2D. Ovary color: 144A.

*Seed/fruit.*—Development of seeds and fruit have not been observed.

Disease/pest resistance: Plants of the new Ivy Geranium have not been observed to be resistant to pathogens and pests common to Ivy Geraniums.

Temperature tolerance: Plants of the new Ivy Geranium have been observed to be tolerant to temperatures ranging from 5 to 40° C.

It is claimed:

1. A new and distinct cultivar of Ivy Geranium plant named 'Duebalila', as herein illustrated and described.

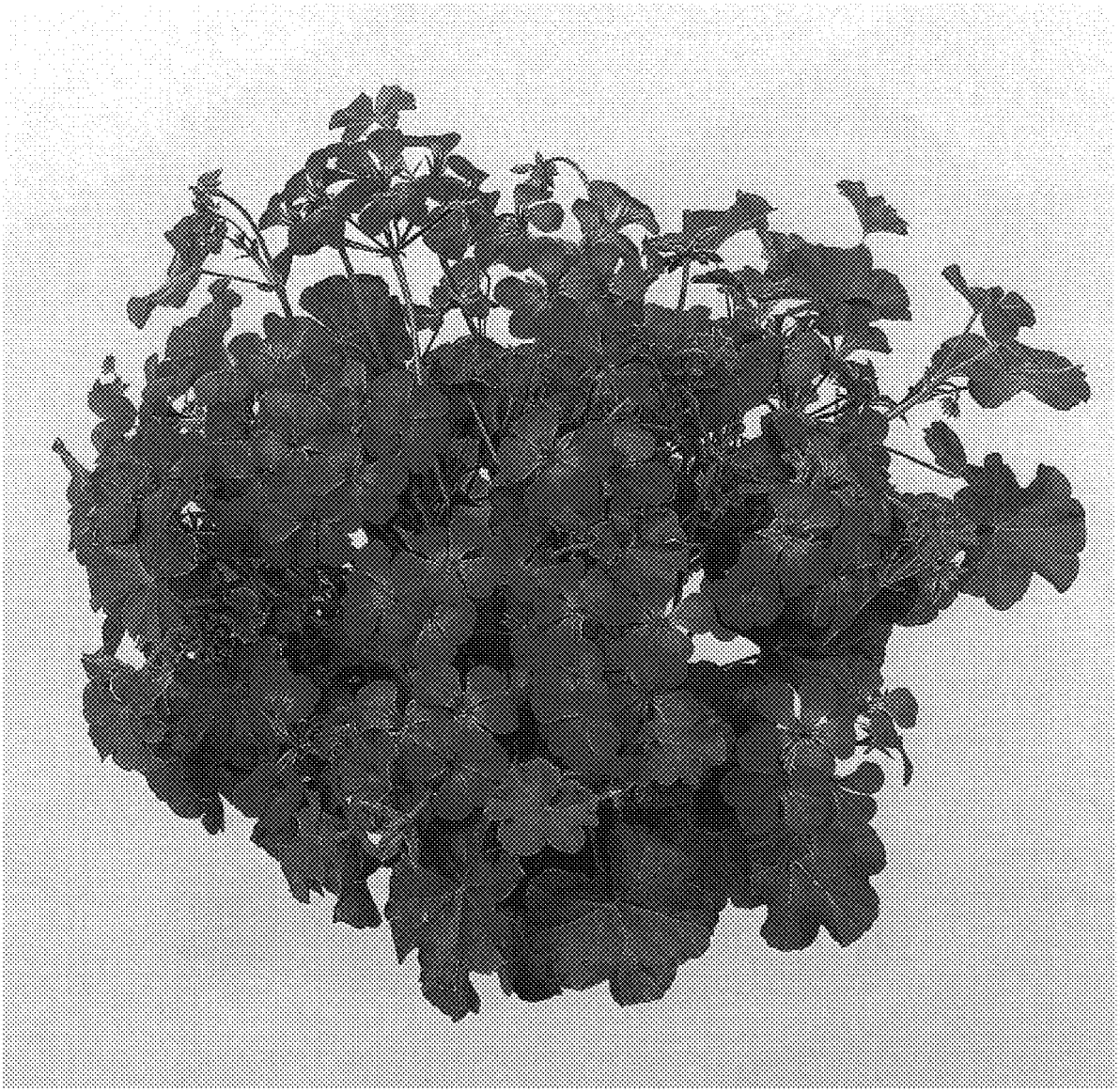

* * * * *